United States Patent
Babbitt et al.

[11] Patent Number: 5,563,516
[45] Date of Patent: Oct. 8, 1996

[54] APPARATUS FOR SENSING AND MEASURING FLOW OF DRY PARTICULATE MATERIAL

[76] Inventors: Stewart L. Babbitt, 302 E. 24th, Houston, Tex. 77008; Damrong Tarukachon, 11111 Bellsprings Dr., Houston, Tex. 77072

[21] Appl. No.: 390,381

[22] Filed: Feb. 17, 1995

Related U.S. Application Data

[62] Division of Ser. No. 275,131, Jul. 13, 1994.

[51] Int. Cl.$^6$ ............................................. G01N 27/60
[52] U.S. Cl. ............................................. 324/454; 73/861.08
[58] Field of Search .......................... 73/861.04, 861.08, 73/861.09; 324/454

[56] References Cited

U.S. PATENT DOCUMENTS

| | | | |
|---|---|---|---|
| 2,787,784 | 4/1957 | Meryman | 324/454 |
| 3,148,541 | 9/1964 | Higgens | 73/861.08 |
| 4,074,184 | 2/1978 | Dechene et al. | |
| 4,082,994 | 4/1978 | Newton | |
| 4,288,741 | 9/1981 | Dechene et al. | |
| 4,291,273 | 9/1981 | Dechene et al. | |
| 4,619,145 | 10/1986 | Girgenti | 73/861.08 |
| 4,631,482 | 12/1986 | Newton et al. | |
| 4,659,218 | 4/1987 | de Lasa | 73/861.04 |
| 4,714,890 | 12/1987 | Dechene et al. | |
| 4,774,453 | 9/1988 | Dechene et al. | |
| 4,904,944 | 2/1990 | Dechene et al. | |

OTHER PUBLICATIONS

Babbitt International, Inc.–"FS 10000 Dry material Flow Switch" Brochure Dec. 1990.
Babbitt International, Inc.–Owners' Manual.

*Primary Examiner*—Maura Regan
*Attorney, Agent, or Firm*—Bush, Moseley, Riddle & Jackson, LLP

[57] ABSTRACT

An improved apparatus for sensing and measuring the flow of dry particulate materials including a sensing device (20C) connected to a remote measuring device by a coaxial cable (25). The sensing device (20C) has a probe (24) defining an electrode which may be positioned within a flow line (18). Particles passing over the probe (24) produce a measurable electrical charge to the probe (24) due to the triboflow effect which may be transmitted to a remote measuring device by a coaxial cable (25). A shield (40) envelopes the probe (24) in a telescoping relation and comprises a wire mesh screen, which permits the flow of dry particulate material over the probe (24) while restricting stray electrical interference and electromagnetic radiation to the probe (24).

8 Claims, 1 Drawing Sheet

APPARATUS FOR SENSING AND MEASURING FLOW OF DRY PARTICULATE MATERIAL

This application is a divisional of Ser. No. 08/275,131, pending filed Jul. 13, 1994.

BACKGROUND OF THE INVENTION

1. Field of the Invention

This invention relates generally to an apparatus for sensing and measuring the flow of dry particulate material, and more particularly to such apparatus including a probe defining an electrode which is adapted for placement within a fluid conduit for sensing the flow of dry particulate material along such fluid conduit. Such particulate material may be tiny in size and not visible to the eye under ordinary lighting conditions.

2. Description of the Prior Art

When dry particulate material or particles impact or rub against an object such as a metal probe, the friction of the particles passing over the probe induces a measurable electrical charge transfer to the surface of the probe. Such charge transfer is known as triboelectric effect. The amount of charge imparted to the probe is related to the flow rate of such particles. By measuring such electrical charge, the existence of the flow and the flow rate of the particles may be determined or sensed. Upon the detection of an excessive flow rate of particles past the probe, a signal such as an audible alarm may be provided, or the signal may be used to control a valve, etc.

To provide accurate measurements of flow, sources of noise charge induced on the probe must be minimized. Stray electrical interference or electromagnetic radiation directed toward the probe can render the measurements of the probe inaccurate. Electrical switches and other equipment in the area such as fans and blowers used in conduits and elsewhere to control the flow of the dry particulate material can emit electromagnetic radiation which can generate noise charges on the probe.

At least two prior art, dry material flow switches are commercially available and are part of the prior art related to the invention. The first is a product designated as FS10000 Dry Material Flow Switch sold by BABBITT International, Inc., of P.O. Box 70094, Houston, Tex. 77270. The FS10000 switch includes a housing and bushing with an electrically insulated rod of stainless steel extending therefrom. The bushing enables the housing to be secured (e.g., by threads) within an opening of a conduit such that the rod extends perpendicularly into the flow path of the conduit. A coaxial cable is conductively attached to the end of the rod within the housing. The coaxial cable, electrically insulated from the housing, runs to a remote charge sensing electrical circuit for producing an alarm or other signal depending on the level of charge sensed on the cable.

The second is a switch designated as Model No. 2100 of Auburn International, Inc. of Eight Electronics Avenue, P.O. Box 2008, Danvers, Mass. Such switch likewise includes a probe extending from a housing, with a bushing provided to screw the housing to an opening in a conduit so that a probe, electrically insulated from the housing, may be inserted perpendicularly into the flow path of the conduit. The probe of the Auburn Model No. 2100 is likewise converted to an electronic sensing device which senses the level of charge transferred to the probe because of the triboelectric effect of dust or small particulate matter flowing against and past the probe in the conduit.

U.S. Pat. No. 4,619,145 dated Oct. 28, 1986 describes apparatus for sensing and measuring the flow of dry particulate material. It recognizes the problem of electrical interference on electrodes or probes for a small diameter critical flow path or passage for dry particulate material. Insulators are provided in the '145 patent for insulating an electrode from electrical interference when such electrode is in contact with the dry particulate material.

SUMMARY OF THE INVENTION

As indicated above, stray or unwanted electromagnetic radiation may affect the amount of charge induced on the probe of prior art dry material flow switches, and thereby result in a premature alarm or signal in such switch thereby erroneously indicating an excessive flow rate in the conduit.

It is important that accurate and precise measurements be obtained from the electrode or probe inserted within the conduit for the particulate material. Thus, the present invention is directed specifically to a means for shielding the electrode or probe of existing dry material flow switches from external electrical interference, such as electromagnetic radiation, yet allowing particulate flow to be relatively unaffected by such shielding.

The object of this invention is to provide a shielded probe for prior art dry material flow switches thereby reducing or eliminating stray electromagnetic induced noise charge and including shielding for the probe by which electrical interference is shielded from the probe while permitting the flow of dry particulate material across the probe.

BRIEF DESCRIPTION OF THE DRAWINGS

Other objects, features, and advantages of this invention will become apparent from the following more detailed description taken in conjunction with the attached drawings in which.

DESCRIPTION OF THE PREFERRED EMBODIMENT OF THE INVENTION

Figure 1:
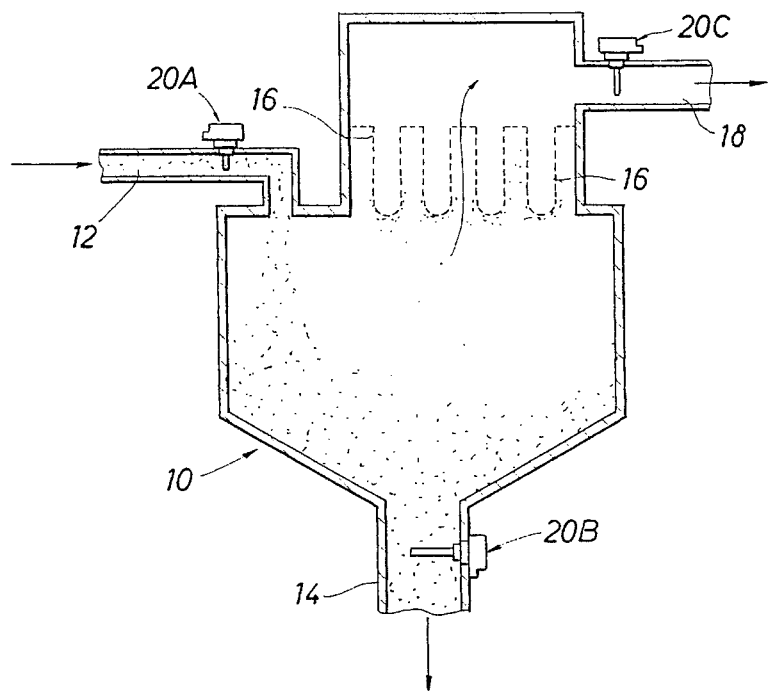
FIG. 1 is a schematic illustration of various applications for prior art dry material flow switch apparatus.

Referring to the drawings for a better understanding of the invention and particularly to FIG. 1 which illustrates typical applications of prior art dry material flow switch apparatus, a hopper or bin is shown generally at 10 for the collection of dry particulate material, such as grain, for loading into containers beneath hopper 10, such as bags or the like. A pneumatic conveying line is shown at 12 for pneumatic conveyance of the dry particulate material into hopper 10. The grain is discharged from the lower end or chute 14 into a suitable container. Dust from hopper 10 is filtered through filter bags 16. Discharge air is passed through discharge line 18.

Typical prior art dry material flow switches are shown at 20A, 20B, and 20C for three separate applications. Each switch 20A, 20B and 20C is identical except for magnitude adjustments to sense varying flow rate levels of dry particulate material. Switch 20A is adjusted for sensing and measuring the flow rate of the dry particulate material through pneumatic line 12 into hopper 10 and to provide an audible signal (or an electrical signal to make a record on a chart recorder or to control a value, or to cause a relay contact to close, etc.) in the event flow stops or decreases below a predetermined minimum. Switch 20B may be adjusted for sensing and measuring the gravity flow of dry particulate material, such as grain, through lower chute 14 and to provide an audible signal when the gravity induced flow rate of the grain is blocked or decreases below a predetermined minimum. Switch 20C is provided in discharge line 16 for dust and other fine particulate material and may be adjusted to provide an audible signal (or electrical signal for control of a valve) when the flow rate of dust and other dry particulate material exceeds a predetermined amount which may occur, for example, upon the rupture of a bag filter 16.

Figure 2:
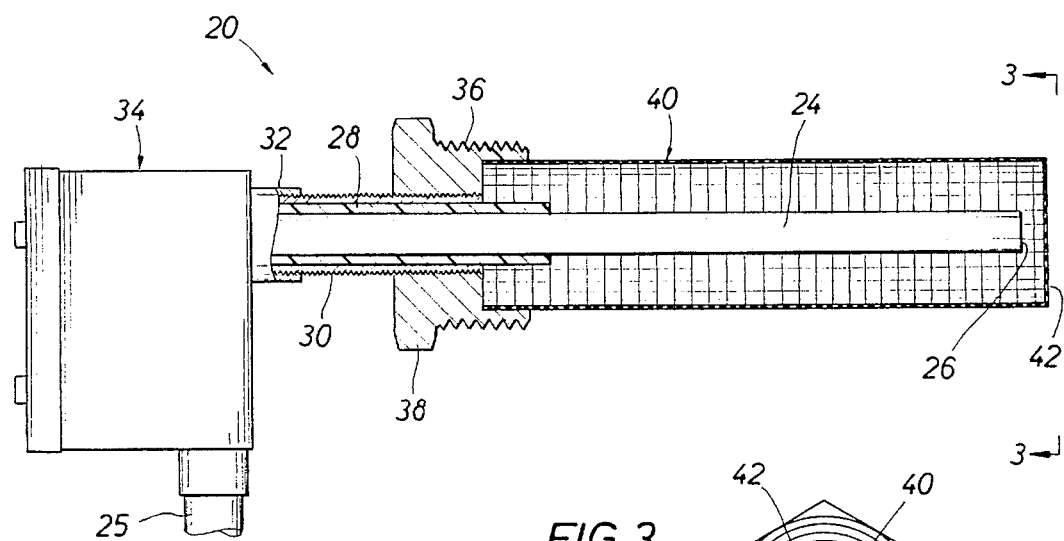
FIG. 2 is a side elevational view of the shielded probe of this invention which is substituted for prior probes of dry material flow switch apparatus.

As shown in FIG. 2, switch 20 includes an elongate probe or rod 24 of a generally cylindrical shalt with an extending free end 26. Probe 24 forms an electrode and is preferably formed of stainless steel, but it may be formed of tungsten carbine or other materials. An insulating sleeve 28 extends about the upper end portion of elongate probe 24 and is preferably formed of a polyethylene material of a high molecular weight. It may also be formed of Teflon brand of polymer. A metallic nipple 30 is externally threaded at its opposite ends with one end threaded within fitting 32 on housing 34. A metallic bushing 36 is threaded both internally and externally for threading on nipple 30 and on a suitable internally threaded fitting of a conduit such as discharge line 18, or input line 12 or hopper exit line 14, etc. (FIG. 1). Bushing 36 has a hexagonal head 38 adjacent such threads for securement with cooperating threads of an opening in a conduit. Probe 24 extends to housing 34, yet is conductively isolated from it. Probe 24 is conductively connected in a conventional manner to coaxial cable 25 for the transmission of electrical signals to the measuring electrical charge level sensing devices of the prior art dry material flow switches as described above.

To prevent stray electromagnetic induced charge on probe 24, a shield generally indicated at 40 and preferably comprising a wire mesh screen is secured, preferably by welding it to the end of bushing 36. Bushing 36 is preferably metallic, as is nipple 30, fitting 32 and housing 34.

In order to obtain a good electrical connection between shield 40 and bushing 36, the interior surface of bushing 36 is machined to produce a smooth surface. Such machining may be necessary for a conventional bushing purchased from a hardware supplier, for example. Next, the screen 40 is electrically connected to the smooth surface of the bushing 36. Connection is made by brazing the shield 40 to bushing 36 with silver solder. Accordingly, the conductive connection between screen 40, bushing 36, nipple 30, fitting 32 and housing 34 insures that the entire probe 24 has a metallic equipotential shield enveloping it from the tip of rod or probe 24 to its connection with coaxial cable 24 within housing 34.

Shield 40 has an outer end 42 which extends beyond the end of probe 24. Shield 40, including its end 42, may be formed of ½ inch mesh galvanized screen, for example. Shield or screen 40 has openings or perforations which are of a size sufficient to permit the flow of dry particulate material through the screen for contacting probe 24 with the friction of the particulate material passing over probe 24 thereby creating triboelectric charge from the moving particles to the surface of probe 24. By measurement of the level of such electrical charge, the flow rate of the dry particulate material may be determined as with prior art dry material flow switches. Stray electrical interference or electromagnetic radiation, caused, for example, by opening and closing electrical switches or by the operation of electrical motors of fans, blowers and the like in proximity with the dry material flow switch, which naturally would induce noise charge on probe 24, is shielded by screen 40 from probe 24. Shielding is also provided from stray currents induced on metallic ducts or static charge or non-metallic (e.g., plastic ducts) in which a dry material flow switch is placed. In this manner, electromagnetic radiation induced noise, as a source of inaccuracy of prior art material flow switches may be minimized.

Figure 4:
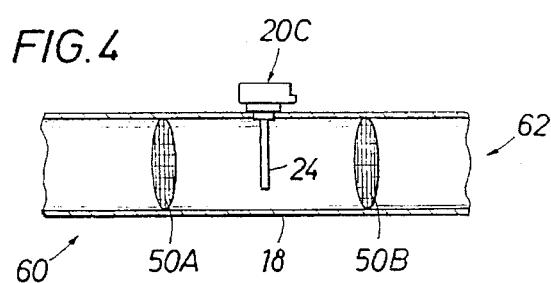
FIG. 4 illustrates an alternative embodiment of the invention where an electromagnetic screen is placed within a metallic duct so as to shield the probe of a dry material flow switch from electromagnetic radiation.
Figure 3:
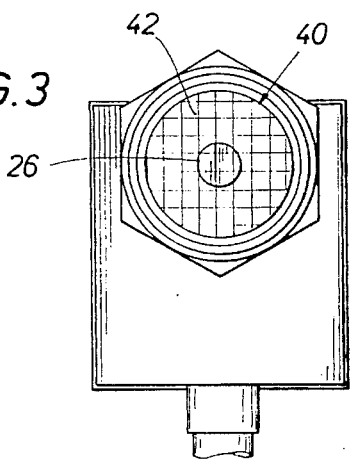
FIG. 3 is an end view of the shielded probe shown in FIG. 2 and looking generally along line 3—3 of FIG. 2.

FIG. 4 illustrates an alternative embodiment of apparatus for shielding the probe 24 of a dry material flow switch in a duct 18, especially a metallic duct. Rather than placing a metallic shield directly about the probe 24 itself, as in FIG. 2, a shield 50A is placed in electrical contact with the duct 18, and in the duct so that electromagnetic radiation approaching from the end 60 at which screen 50A is placed is prevented from reaching probe 24. The mesh of shield 50A is of a size similar to that described above with respect to shield 40 placed about probe 24 as illustrated in FIG. 2. In other words, the openings of the mesh are large enough so as to not inhibit free flow of dry particulate material through it, but the metallic mesh is small enough to provide effective shielding from currents and noise induced on the metallic duct 18. Mesh 50A serves to shield probe 24 from electromagnetic radiation flow on end 60 of duct 18. Preferably a second mesh shield in the duct 18 as illustrated at 50B, is provided on the other side of probe 24 to shield probe 24 from radiation via the other end 62 of duct 18.

Since certain changes or modifications may be made in the disclosed embodiment without departing from the inventive concepts involved, it is the aim of the appended claims to cover all such changes and modifications falling within the true spirit and scope of the present invention.

What is claimed is:

1. A system for measuring the flow rate of dry particulate material comprising:

a metallic duct positioned to provide a flow path for dry particulate material;

a dry material flow switch having a probe extending into said flow path of said duct; and metallic mesh means for shielding said probe from electromagnetic radiation in said duct.

2. The system of claim 1 wherein:

said dry material flow switch includes a metallic bushing for securing said switch to said duct; and said metallic mesh means includes a cylindrical mesh structure electrically connected to said metallic bushing.

3. The system of claim 2 wherein:

said cylindrical mesh structure includes an end mesh structure electrically connected to said cylindrical mesh structure so that said probe is entirely surrounded within said duct by metallic mesh so that said metallic mesh cylindrical structure and said end mesh structure shield said probe from electromagnetic radiation within said duct while permitting free flow of dry particulate material through said duct and across said probe.

4. The system of claim 1 wherein said metallic mesh means includes a mesh structure sized and dimensioned to fit within the interior of the duct, said mesh structure having a side positioned in proximity with a first side of said probe of said flow switch, said mesh structure being electrically connected to said metallic duct for shielding said probe from electromagnetic radiation emanating from the other side of said mesh structure within said duct.

5. The system of claim 4 further comprising:

a second mesh structure sized and dimensioned to fit within the interior of the duct, said second mesh structure having a first side positioned in proximity with a second side of said probe of said flow switch, said second mesh structure being electrically connected to said metallic duct for shielding said probe from electromagnetic radiation emanating from the other side of said second mesh structure within said duct.

6. A system for measuring the flow rate of dry particulate material comprising:

a duct positioned to provide a flow path for dry particulate material, said duct having an opening sized and arranged to accept a dry material flow sensor;

a dry material flow sensor having a probe disposed within said duct and a metallic housing disposed outside said duct where said probe extends from said housing via said opening of said duct;

means for electrically insulating said probe from said housing; and metallic mesh means electrically connected to said housing for shielding said probe from electromagnetic radiation.

7. The system of claim 6 wherein said duct is made of a non-metallic material.

8. The system of claim 6 wherein said duct is made of a metallic material and wherein said metallic housing of said sensor is electrically connected to said metallic material of said duct.

* * * * *